US009835566B2

(12) United States Patent
Liang et al.

(10) Patent No.: US 9,835,566 B2
(45) Date of Patent: Dec. 5, 2017

(54) ADAPTIVE NUISANCE FILTER

(71) Applicant: KLA-Tencor Corporation, Milpitas, CA (US)

(72) Inventors: Ardis Liang, Pleasanton, CA (US); Martin Plihal, Pleasanton, CA (US); Raghav Babulnath, San Jose, CA (US); Sankar Venkataraman, Milpitas, CA (US)

(73) Assignee: KLA-Tencor Corp., Milpitas, CA (US)

( * ) Notice: Subject to any disclaimer, the term of this patent is extended or adjusted under 35 U.S.C. 154(b) by 0 days.

(21) Appl. No.: 15/058,115

(22) Filed: Mar. 1, 2016

(65) Prior Publication Data
US 2016/0258879 A1 Sep. 8, 2016

Related U.S. Application Data

(60) Provisional application No. 62/127,583, filed on Mar. 3, 2015.

(51) Int. Cl.
*G01N 21/88* (2006.01)
*G01N 23/20* (2006.01)
*G01N 21/95* (2006.01)

(52) U.S. Cl.
CPC ..... *G01N 21/8806* (2013.01); *G01N 21/9501* (2013.01); *G01N 23/20008* (2013.01);
(Continued)

(58) Field of Classification Search
CPC ........... G01N 21/8806; G01N 21/9501; G01N 23/20008; G01N 2021/8809;
(Continued)

(56) References Cited

U.S. PATENT DOCUMENTS 7,747,062 B2 6/2010 Chen et al.
8,135,204 B1 * 3/2012 Chen .................. G01N 21/9501
250/310
(Continued)

FOREIGN PATENT DOCUMENTS

WO 2014/028513 2/2014

OTHER PUBLICATIONS

International Search Report for PCT/US2016/020772 dated Jun. 7, 2016.
(Continued)

*Primary Examiner* — Sang Nguyen
(74) *Attorney, Agent, or Firm* — Ann Marie Mewherter

(57) ABSTRACT

Methods and systems for generating inspection results for a specimen with an adaptive nuisance filter are provided. One method includes selecting a portion of events detected during inspection of a specimen having values for at least one feature of the events that are closer to at least one value of at least one parameter of the nuisance filter than the values for at least one feature of another portion of the events. The method also includes acquiring output of an output acquisition subsystem for the sample of events, classifying the events in the sample based on the acquired output, and determining if one or more parameters of the nuisance filter should be modified based on results of the classifying. The nuisance filter or the modified nuisance filter can then be applied to results of the inspection of the specimen to generate final inspection results for the specimen.

27 Claims, 2 Drawing Sheets

(52) U.S. Cl.
CPC ............... *G01N 2021/8809* (2013.01); *G01N 2201/061* (2013.01); *G01N 2201/0683* (2013.01)

(58) Field of Classification Search
CPC ..... G01N 2201/061; G01N 2201/0683; G05B 23/0221; G06T 7/0004
See application file for complete search history.

(56) References Cited

U.S. PATENT DOCUMENTS

| | | | |
|---|---|---|---|
| 8,664,594 B1 | 3/2014 | Jiang et al. | |
| 8,692,204 B2 | 4/2014 | Kojima et al. | |
| 8,698,093 B1 | 4/2014 | Gubbens et al. | |
| 8,716,662 B1 | 5/2014 | MacDonald et al. | |
| 9,201,022 B2 * | 12/2015 | Hu | G01N 21/9501 |
| 2005/0111727 A1 | 5/2005 | Emery | |
| 2006/0115143 A1 | 6/2006 | Auerbach | |
| 2006/0287751 A1 * | 12/2006 | Dishner | G05B 23/0221 |
| | | | 700/110 |
| 2007/0156379 A1 | 7/2007 | Kulkarni et al. | |
| 2007/0286473 A1 * | 12/2007 | Leslie | G01N 21/9501 |
| | | | 382/146 |
| 2009/0080759 A1 | 3/2009 | Bhaskar et al. | |
| 2009/0297019 A1 | 12/2009 | Zafar et al. | |
| 2014/0050389 A1 | 2/2014 | Mahadevan et al. | |
| 2014/0133737 A1 * | 5/2014 | Plihal | G06T 7/0008 |
| | | | 382/149 |
| 2014/0301630 A1 | 10/2014 | Kulkarni et al. | |
| 2015/0043804 A1 * | 2/2015 | Huang | G06T 7/0006 |
| | | | 382/149 |
| 2015/0179400 A1 | 6/2015 | Lauber | |

OTHER PUBLICATIONS

Written Opinion for PCT/US2016/020772 dated Jun. 7, 2016.
International Search Report for PCT/US2016/020762 dated Jun. 14, 2016.

* cited by examiner

ADAPTIVE NUISANCE FILTER

BACKGROUND OF THE INVENTION

1. Field of the Invention

This invention generally relates to methods and systems for generating inspection results for a specimen with an adaptive nuisance filter.

2. Description of the Related Art

The following description and examples are not admitted to be prior art by virtue of their inclusion in this section.

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a single semiconductor wafer and then separated into individual semiconductor devices.

Inspection processes are used at various steps during a semiconductor manufacturing process to detect defects on wafers. Inspection processes have always been an important park of fabricating semiconductor devices such as integrated circuits. However, as the dimensions of semiconductor devices decrease, inspection processes become even more important to the successful manufacture of acceptable semiconductor devices. For instance, as the dimensions of semiconductor devices decrease, detection of defects of decreasing size has become necessary since even relatively small defects may cause unwanted aberrations in the semiconductor devices.

Inspection generally involves generating some output (e.g., images, signals, etc.) for a wafer by directing light or electrons to the wafer and detecting the light or electrons from the wafer. Once the output has been generated, defect detection is typically performed by applying some defect detection method and/or algorithm to the output. Parameters used to generate the output (e.g., optical or electron beam hardware settings), parameters used to detect the defects (e.g., defect detection algorithm settings), and any other parameters used to generate the inspection results (e.g., nuisance filter algorithm settings) are typically determined based on characteristics of the wafer and defects to be detected thereon. Most often, the goal of inspection recipe setup is to determine the parameters that will provide the highest sensitivity to defects of interest while suppressing detection of nuisance and noise on the wafer.

Inspection recipe set up can be performed in a number of different manners. For example, an inspection recipe can be trained on one or a few training wafers. However, once the inspection recipe has been generated, typically, the static inspection recipe is used indefinitely. For example, once an inspection recipe has been generated, it will typically be used indefinitely while monitoring manually the stability of the recipe, e.g., in production. Manual re-tuning of the inspection recipe may be performed when necessary. There are, however, a number of disadvantages to such approaches for using and monitoring inspection recipes. For example, the inspection recipe cannot be adjusted dynamically to process variations, tends to be unstable with respect to the nuisance rate, and can only be monitored manually.

Accordingly, it would be advantageous to develop systems and/or methods for generating inspection results for a specimen with an adaptive nuisance filter that do not have one or more of the disadvantages described above.

SUMMARY OF THE INVENTION

The following description of various embodiments is not to be construed in any way as limiting the subject matter of the appended claims.

One embodiment relates to a system configured to generate inspection results for a specimen with an adaptive nuisance filter. The system includes an output acquisition subsystem that includes at least an energy source and a detector. The energy source is configured to generate energy that is directed to a specimen. The detector is configured to detect energy from the specimen and to generate output responsive to the detected energy. The system also includes one or more computer subsystems configured for acquiring results of an inspection of the specimen and parameters of a nuisance filter for the inspection. The results include values for one or more features for events detected during the inspection. The values are determined during the inspection. The computer subsystem(s) are also configured for generating a sample of the events by selecting a portion of the events having the values for at least one of the one or more features that are closer to at least one value of at least one of the parameters of the nuisance filter than the values for the at least one of the one or more features of another portion of the events. In addition, the computer subsystem(s) are configured for acquiring the output of the output acquisition subsystem for the sample of the events and classifying the events in the sample based on the acquired output.

The computer subsystem(s) are further configured for determining if one or more of the parameters of the nuisance filter should be modified based on results of the classifying. When it is determined that the one or more of the parameters of the nuisance filter should not be modified, the computer subsystem(s) are configured for applying the nuisance filter to the results of the inspection for the specimen to generate final inspection results for the specimen. When it is determined that the one or more of the parameters of the nuisance filter should be modified, the computer subsystem(s) are configured for modifying the nuisance filter by modifying the one or more of the parameters of the nuisance filter based on the results of the classifying and applying the modified nuisance filter to the results of the inspection for the specimen to generate the final inspection results for the specimen. The system may be further configured as described herein.

Another embodiment relates to a computer-implemented method for generating inspection results for a specimen with an adaptive nuisance filter. The method includes steps for each of the functions of the one or more computer subsystems described above. The steps of the method are performed by one or more computer subsystems. The method may be performed as described further herein. In addition, the method may include any other step(s) of any other method(s) described herein. Furthermore, the method may be performed by any of the systems described herein.

An additional embodiment relates to a non-transitory computer-readable medium storing program instructions executed on a computer system for performing a computer-implemented method for generating inspection results for a specimen with an adaptive nuisance filter. The computer-implemented method includes the steps of the method described above. The computer-readable medium may be further configured as described herein. The steps of the computer-implemented method may be performed as described further herein. In addition, the computer-implemented method for which the program instructions are executable may include any other step(s) of any other method(s) described herein.

BRIEF DESCRIPTION OF THE DRAWINGS

Other objects and advantages of the invention will become apparent upon reading the following detailed description and upon reference to the accompanying drawings in which.

Figure 1:
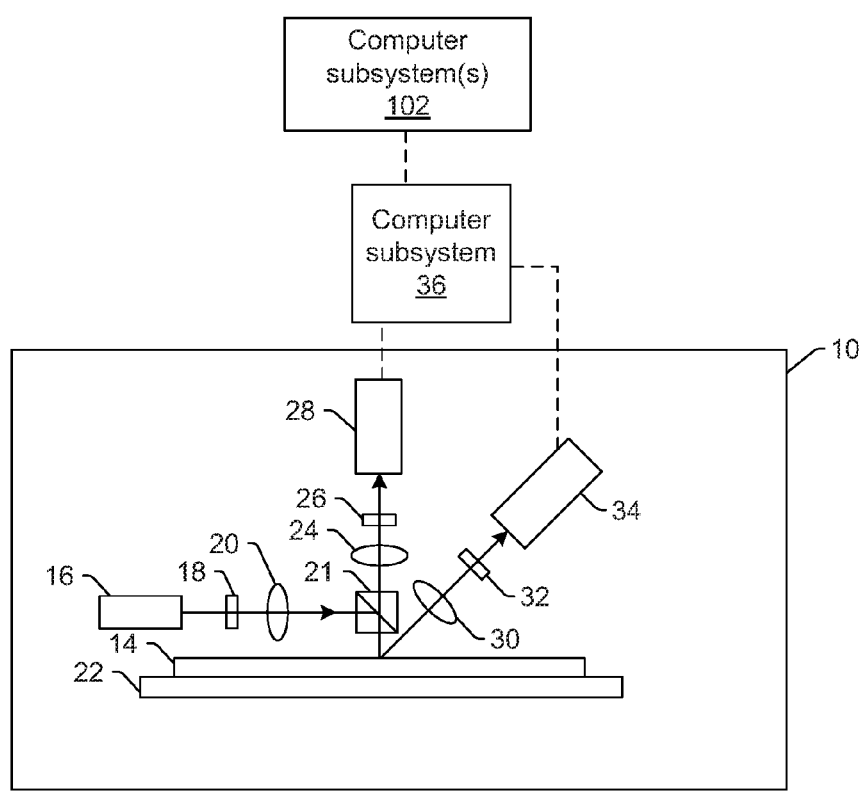
FIGS. 1 and 2 are schematic diagrams illustrating side views of embodiments of a system configured as described herein.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals. Unless otherwise noted herein, any of the elements described and shown may include any suitable commercially available elements.

One embodiment relates to a system configured to generate inspection results for a specimen with an adaptive nuisance filter. As described further herein, the embodiments provide new ways for tuning and applying nuisance filters to the results of inspection (e.g., optical or electron beam inspection). As also described further herein, the embodiments advantageously increase stability of inspections (such as optical inspections) with respect to the nuisance rate and defect of interest (DOI) capture and make it possible to monitor process variations that are responsible for recipe instabilities in inspections.

In one embodiment, the specimen includes a wafer. In another embodiment, the specimen includes a reticle. The wafer and the reticle may include any wafer and reticle known in the art.

One embodiment of such a system is shown in FIG. 1. The system includes an output acquisition subsystem that includes at least an energy source and a detector. The energy source is configured to generate energy that is directed to a specimen. The detector is configured to detect energy from the specimen and to generate output responsive to the detected energy.

In one embodiment, the energy directed to the specimen includes light, and the energy detected from the specimen includes light. For example, in the embodiment of the system shown in FIG. 1, output acquisition subsystem 10 includes an illumination subsystem configured to direct light to specimen 14. The illumination subsystem includes at least one light source. For example, as shown in FIG. 1, the illumination subsystem includes light source 16. In one embodiment, the illumination subsystem is configured to direct the light to the specimen at one or more angles of incidence, which may include one or more oblique angles and/or one or more normal angles. For example, as shown in FIG. 1, light from light source 16 is directed through optical element 18 and then lens 20 to beam splitter 21, which directs the light to specimen 14 at a normal angle of incidence. The angle of incidence may include any suitable angle of incidence, which may vary depending on, for instance, characteristics of the specimen and the defects to be detected on the specimen.

The illumination subsystem may be configured to direct the light to the specimen at different angles of incidence at different times. For example, the output acquisition subsystem may be configured to alter one or more characteristics of one or more elements of the illumination subsystem such that the light can be directed to the specimen at an angle of incidence that is different than that shown in FIG. 1. In one such example, the output acquisition subsystem may be configured to move light source 16, optical element 18, and lens 20 such that the light is directed to the specimen at a different angle of incidence.

In some instances, the output acquisition subsystem may be configured to direct light to the specimen at more than one angle of incidence at the same time. For example, the illumination subsystem may include more than one illumination channel, one of the illumination channels may include light source 16, optical element 18, and lens 20 as shown in FIG. 1 and another of the illumination channels (not shown) may include similar elements, which may be configured differently or the same, or may include at least a light source and possibly one or more other components such as those described further herein. If such light is directed to the specimen at the same time as the other light, one or more characteristics (e.g., wavelength, polarization, etc.) of the light directed to the specimen at different angles of incidence may be different such that light resulting from illumination of the specimen at the different angles of incidence can be discriminated from each other at the detector(s).

In another instance, the illumination subsystem may include only one light source (e.g., source 16 shown in FIG. 1) and light from the light source may be separated into different optical paths (e.g., based on wavelength, polarization, etc.) by one or more optical elements (not shown) of the illumination subsystem. Light in each of the different optical paths may then be directed to the specimen. Multiple illumination channels may be configured to direct light to the specimen at the same time or at different times (e.g., when different illumination channels are used to sequentially illuminate the specimen). In another instance, the same illumination channel may be configured to direct light to the specimen with different characteristics at different times. For example, in some instances, optical element 18 may be configured as a spectral filter and the properties of the spectral filter can be changed in a variety of different ways (e.g., by swapping out the spectral filter) such that different wavelengths of light can be directed to the specimen at different times. The illumination subsystem may have any other suitable configuration known in the art for directing the light having different or the same characteristics to the specimen at different or the same angles of incidence sequentially or simultaneously.

In one embodiment, light source 16 may include a broadband plasma (BBP) light source. In this manner, the light generated by the light source and directed to the specimen may include broadband light. However, the light source may include any other suitable light source such as a laser. The laser may include any suitable laser known in the art and may be configured to generate light at any suitable wavelength or wavelengths known in the art. In addition, the laser may be configured to generate light that is monochromatic or nearly-monochromatic. In this manner, the laser may be a narrowband laser. The light source may also include a polychromatic light source that generates light at multiple discrete wavelengths or wavebands.

Light from optical element 18 may be focused to beam splitter 21 by lens 20. Although lens 20 is shown in FIG. 1 as a single refractive optical element, it is to be understood that, in practice, lens 20 may include a number of refractive and/or reflective optical elements that in combination focus the light from the optical element to the specimen. The illumination subsystem shown in FIG. 1 and described herein may include any other suitable optical elements (not shown). Examples of such optical elements include, but are not limited to, polarizing component(s), spectral filter(s), spatial filter(s), reflective optical element(s), apodizer(s), beam splitter(s), aperture(s), and the like, which may include any such suitable optical elements known in the art. In addition, the system may be configured to alter one or more of the elements of the illumination subsystem based on the type of illumination to be used for output acquisition.

The output acquisition subsystem may also include a scanning subsystem configured to cause the light to be scanned over the specimen. For example, the output acquisition subsystem may include stage 22 on which specimen 14 is disposed during output acquisition. The scanning subsystem may include any suitable mechanical and/or robotic assembly (that includes stage 22) that can be configured to move the specimen such that the light can be scanned over the specimen. In addition, or alternatively, the output acquisition subsystem may be configured such that one or more optical elements of the output acquisition subsystem perform some scanning of the light over the specimen. The light may be scanned over the specimen in any suitable fashion.

The output acquisition subsystem further includes one or more detection channels. At least one of the one or more detection channels includes a detector configured to detect light from the specimen due to illumination of the specimen by the output acquisition subsystem and to generate output responsive to the detected light. For example, the output acquisition subsystem shown in FIG. 1 includes two detection channels, one formed by collector 24, element 26, and detector 28 and another formed by collector 30, element 32, and detector 34. As shown in FIG. 1, the two detection channels are configured to collect and detect light at different angles of collection. In some instances, one detection channel is configured to detect specifically reflected light, and the other detection channel is configured to detect light that is not specularly reflected (e.g., scattered, diffracted, etc.) from the specimen. However, two or more of the detection channels may be configured to detect the same type of light from the specimen (e.g., specularly reflected light). Although FIG. 1 shows an embodiment of the output acquisition subsystem that includes two detection channels, the output acquisition subsystem may include a different number of detection channels (e.g., only one detection channel or two or more detection channels). Although each of the collectors are shown in FIG. 1 as single refractive optical elements, it is to be understood that each of the collectors may include one or more refractive optical element(s) and/or one or more reflective optical element(s).

The one or more detection channels may include any suitable detectors known in the art. For example, the detectors may include photo-multiplier tubes (PMTs), charge coupled devices (CCDs), and time delay integration (TDI) cameras. The detectors may also include any other suitable detectors known in the art. The detectors may also include non-imaging detectors or imaging detectors. In this manner, if the detectors are non-imaging detectors, each of the detectors may be configured to detect certain characteristics of the scattered light such as intensity but may not be configured to detect such characteristics as a function of position within the imaging plane. As such, the output that is generated by each of the detectors included in each of the detection channels of the output acquisition system may be signals or data, but not image signals or image data. In such instances, a computer subsystem such as computer subsystem 36 of the system may be configured to generate images of the specimen from the non-imaging output of the detectors. However, in other instances, the detectors may be configured as imaging detectors that are configured to generate imaging signals or image data. Therefore, the system may be configured to generate the output described herein in a number of ways.

It is noted that FIG. 1 is provided herein to generally illustrate a configuration of an output acquisition subsystem that may be included in the system embodiments described herein. Obviously, the output acquisition subsystem configuration described herein may be altered to optimize the performance of the system as is normally performed when designing a commercial inspection or defect review system. In addition, the systems described herein may be implemented using an existing output acquisition system (e.g., by adding functionality described herein to an existing output acquisition system) such as optical inspection and/or defect review tools such as the 28xx and 29xx series of tools that are commercially available from KLA-Tencor, Milpitas, Calif., and other tools that are commercially available from other sources. For some such systems, the methods described herein may be provided as optional functionality of the system (e.g., in addition to other functionality of the system). Alternatively, the system described herein may be designed "from scratch" to provide a completely new system.

Computer subsystem 36 of the system may be coupled to the detectors of the output acquisition subsystem in any suitable manner (e.g., via one or more transmission media, which may include "wired" and/or "wireless" transmission media) such that the computer subsystem can receive the output generated by the detectors during scanning of the specimen. Computer subsystem 36 may be configured to perform a number of functions using the output of the detectors as described herein and any other functions described further herein. This computer subsystem may be further configured as described herein.

This computer subsystem (as well as other computer subsystems described herein) may also be referred to herein as computer system(s). Each of the computer subsystem(s) or system(s) described herein may take various forms, including a personal computer system, image computer, mainframe computer system, workstation, network appliance, Internet appliance, or other device. In general, the term "computer system" may be broadly defined to encompass any device having one or more processors, which executes instructions from a memory medium. The computer subsystem(s) or system(s) may also include any suitable processor known in the art such as a parallel processor. In addition, the computer subsystem(s) or system(s) may include a computer platform with high speed processing and software, either as a standalone or a networked tool.

If the system includes more than one computer subsystem, then the different computer subsystems may be coupled to each other such that images, data, information, instructions, etc. can be sent between the computer subsystems as described further herein. For example, computer subsystem 36 may be coupled to computer subsystem(s) 102 (as shown by the dashed line in FIG. 1) by any suitable transmission media, which may include any suitable wired and/or wireless transmission media known in the art. Two or more of such computer subsystems may also be effectively coupled by a shared computer-readable storage medium (not shown).

Although the output acquisition subsystem is described above as being an optical or light-based output acquisition subsystem, the output acquisition subsystem may be an electron beam-based output acquisition subsystem. For example, in one embodiment, the energy directed to the specimen includes electrons, and the energy detected from the specimen includes electrons. In this manner, the energy source may be an electron beam source. In one such embodiment shown in FIG. 2, the output acquisition subsystem includes electron column 122, which is coupled to computer subsystem 124.

Figure 2:
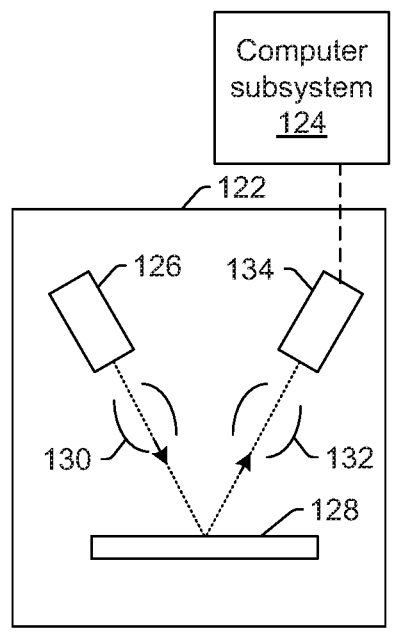

As also shown in FIG. 2, the electron column includes electron beam source 126 configured to generate electrons that are focused to specimen 128 by one or more elements 130. The electron beam source may include, for example, a cathode source or emitter tip, and one or more elements 130 may include, for example, a gun lens, an anode, a beam limiting aperture, a gate valve, a beam current selection aperture, an objective lens, and a scanning subsystem, all of which may include any such suitable elements known in the art.

Electrons returned from the specimen (e.g., secondary electrons may be focused by one or more elements 132 to detector 134. One or more elements 132 may include, for example, a scanning subsystem, which may be the same scanning subsystem included in element(s) 130.

The electron column may include any other suitable elements known in the art. In addition, the electron column may be further configured as described in U.S. Pat. No. 8,664,594 issued Apr. 4, 2014 to Jiang et al., U.S. Pat. No. 8,692,204 issued Apr. 8, 2014 to Kojima et al., U.S. Pat. No. 8,698,093 issued Apr. 15, 2014 to Gubbens et al., and U.S. Pat. No. 8,716,662 issued May 6, 2014 to MacDonald et al., which are incorporated by reference as if fully set forth herein.

Although the electron column is shown in FIG. 2 as being configured such that the electrons are directed to the specimen at an oblique angle of incidence and are scattered from the specimen at another oblique angle, it is to be understood that the electron beam may be directed to and scattered from the specimen at any suitable angles. In addition, the electron beam-based subsystem may be configured to use multiple modes to generate images of the specimen (e.g., with different illumination angles, collection angles, etc.). The multiple modes of the electron beam-based subsystem may be different in any image generation parameters of the subsystem.

Computer subsystem 124 may be coupled to detector 134 as described above. The detector may detect electrons returned from the surface of the specimen thereby forming electron beam images of the specimen. The electron beam images may include any suitable electron beam images. Computer subsystem 124 may be configured to perform any of the functions described herein using the output of the detector and/or the electron beam images. Computer subsystem 124 may be configured to perform any additional step(s) described herein. A system that includes the output acquisition subsystem shown in FIG. 2 may be further configured as described herein.

It is noted that FIG. 2 is provided herein in generally illustrate a configuration of an electron beam-based output acquisition subsystem that may be included in the embodiments described herein. As with the optical output acquisition subsystem described above, the electron beam-based output acquisition subsystem configuration described herein may be altered to optimize the performance of the output acquisition subsystem as is normally performed when designing a commercial inspection or defect review system. In addition, the systems described herein may be implemented using an existing inspection or defect review system (e.g., by adding functionality described herein to an existing inspection or defect review system) such as the eDR-xxxx series of tools that are commercially available from KLA-Tencor. For some such systems, the methods described herein may be provided as optional functionality of the system (e.g., in addition to other functionality of the system). Alternatively, the system described herein may be designed "from scratch" to provide a completely new system.

Although the output acquisition subsystem is described above as being a light- or electron beam-based output acquisition subsystem, the output acquisition subsystem may be an ion beam-based output acquisition subsystem. Such an output acquisition subsystem may be configured as shown in FIG. 2 except that the electron beam source may be replaced with any suitable ion beam source known in the art. In addition, the output acquisition subsystem may be any other suitable ion beam-based subsystem such as those included in commercially available focused ion beam (FIB) systems, helium ion microscopy (HIM) systems, and secondary ion mass spectroscopy (SIMS) systems.

In some instances, inspection of the specimen may be performed by an optical inspection system. For example, an optical output acquisition subsystem such as that described above may be configured for inspection rather than defect review. In such instances, post-inspection output acquisition may be performed by an optical output acquisition subsystem having one or more different parameters than the optical output acquisition subsystem used for inspection (e.g., such that the optical output acquisition subsystem used for post-inspection has a higher resolution than the output acquisition subsystem used for inspection). Alternatively, post-inspection output acquisition may be performed by an electron beam output acquisition subsystem. However, inspection and post-inspection processes may be performed with electron beam based output acquisition subsystems, having different configurations that make them more suitable for the processes in which they will be used. In this manner, in some embodiments, the system includes one of the output acquisition subsystems described herein, and inspection of the specimen is performed with another output acquisition subsystem having a configuration different than the output acquisition subsystem. For example, the system embodiments described herein may be configured as defect review tools that are different from inspection tools. In one particular example, the system embodiments described herein may be configured as scanning electron microscope (SEM) review stations that are different from optical inspection tools used to perform the inspection of the specimen.

The one or more computer subsystems described further herein may be coupled to the output acquisition subsystem that performs inspection of the specimen. Alternatively, other one or more computer subsystems may be coupled to the output acquisition subsystem that performs inspection of the specimen. Such computer subsystem(s) may be configured as described further herein. In any case, one or more computer subsystems coupled to the output acquisition subsystem used for inspection are configured for detecting events on the specimen based on the output generated by one or more detectors of the output acquisition subsystem. The events may be detected on the specimen in any suitable manner (e.g., by applying a threshold to the output and identifying output having one or more values above the threshold as an event (e.g., a defect or potential defect) and not identifying output having one or more values below the threshold as an event. The events detected on the specimen may include any defects, potential defects, nuisance events, etc. known in the art.

In one embodiment, the inspection of the specimen is performed with defect detection parameters selected such that the events detected by the inspection include a substantial amount of nuisance events. In other words, the inspection, for which the results are acquired as described further herein, is preferably configured for producing highly defective initial inspection results. In this manner, the inspection may be run hotter than tuned. In other words, the inspection can be run quite a bit more aggressively (hotter), which means with substantially aggressive defect detection thresholds, so that more events, including defects and nuisance events, are detected than desired in a tuned inspection. In this manner, such an inspection would not be useful for production monitoring due to the substantially high nuisance event detection. Such an inspection is commonly referred to as a "hot" inspection.

Such an inspection may be performed in a manner consistent with a tuned nuisance filter, e.g., event detection parameters may be moved into the noise floor by an amount that would guarantee that all parameters of the nuisance filter can be tuned as described further herein while also preferably ensuring that the number of detected events does not prevent the inspection from being completed (as in an inspection "blow up"). For example, when an inspection blows up, it means that the detected defectivity is so high that the system cannot handle it and typically the inspection is aborted or defects get randomly dropped to achieve acceptable levels. Detecting more defects than is desired in a tuned inspection is important for the embodiments described herein because values for features of DOIs can move up or down with respect to the tuned parameters of the nuisance filter. Therefore, detecting more defects than normal will provide access to defects that would normally end up below the detection threshold in a tuned inspection. The degree to which the inspection is performed hot can be initially determined during training, but it can also be dynamically adjusted.

A recipe used for a hot inspection may be created by an optical or other inspection system. In addition, the optical or other inspection system may generate the hot inspection results without applying a nuisance filter to any of the results of the hot inspection.

Event or defect detection is different than nuisance filtering in a number of important ways. For example, event detection operates typically on the pixels or other output of the detector(s) of the inspection system. Once events have been detected, values for features of the events may be determined based on the output of the detector(s). A nuisance filter may then operate on those feature values to separate detected events that are nuisance events from detected events that are DOIs.

In this manner, the computer subsystem(s) included in the systems described herein do not necessarily generate the results of inspection. For example, the computer subsystem(s) may be configured to acquire results of an inspection of the specimen and parameters of a nuisance filter for the inspection. A user may select the results file to be used by the computer subsystem(s). The parameters of the nuisance filter acquired by the computer subsystem(s) may include any parameters of the nuisance filter such as a template for the nuisance filter and/or one or more classification boundaries or cut-lines for the nuisance filter. In addition, the nuisance filter may be any of the nuisance filters described herein such as a nuisance filter that is tuned on a training wafer. Furthermore, the nuisance filter that is dynamically updated by the embodiments described herein may include any type of nuisance filter known in the art. For example, the nuisance filter may be a decision tree-based nuisance filter.

In one embodiment, the inspection does not include applying the nuisance filter to any of the results of the inspection. For example, applying the nuisance filter may be delayed until after the computer subsystem(s) described herein determine if the nuisance filter should be modified or not, which may be performed as described further herein. In this manner, unlike currently used inspection processes in which nuisance filtering is performed after inspection, in the embodiments described herein, nuisance filtering is not performed until after additional output is generated and acquired for the specimen (e.g., during review-like output generation performed by a system described herein, which may be configured as a defect review tool) and additional steps are performed using that output.

The results include values for one or more features for events detected during the inspection, and the values are determined during the inspection. The one or more features may include any features that can be determined by an inspection system or from results generated by an inspection system. Examples of suitable features that can be used as described further herein include, but are not limited to, energy, magnitude, die coordinates, and design attributes. The results may include any other suitable information about the events detected on the specimen such as the locations of the events detected on the specimen and image data or images generated for the events.

The computer subsystem(s) are also configured for generating a sample of the events by selecting a portion of the events having the values for at least one of the one or more features that are closer to at least one value of at least one of the parameters of the nuisance filter than the values for the at least one of the one or more features of another portion of the events. In one embodiment, the at least one of the parameters of the nuisance filter include a boundary separating one type of the events from another type of the events. For example, the events having one or more values in the vicinity of the original nuisance filter cut-lines or classification boundaries may be selected for inclusion in the portion of the events that makes up the sample. In this manner, the computer subsystem(s) may use information about a nuisance filter to sample the events detected by an inspection of a specimen. In other words, the sampling described herein leverages information about the initially tuned (e.g., supervised tuned) nuisance filter to select the events for further processing described herein. In one such example, the sample may be targeted at the tuned classification boundaries of the nuisance filter for maximum sampling efficiency. In this manner, the sample of the events may be generated based on results produced for previous specimens, including the parameters of the nuisance filter that worked well before. In addition, the sample may be concentrated around the existing cut-lines or classification boundaries of the trained nuisance filter to get information about the most relevant defects, which may be known a prior e.g., from initial recipe tuning, which may be performed on a training specimen), for re-tuning the trained nuisance filter (i.e., those defects or nuisance events having feature values closest to the feature value boundaries in the nuisance filter). For example, when a classification boundary of a nuisance filter has a first value for an event feature, a range of values may be defined around that first value that encompass feature values that can be considered relatively close to the first value. The events having feature values within that range of values may be identified, and all (or a portion of) the events having values within that range may be selected for inclusion in the sample. Similar steps may be performed to sample events that are near any other classification boundaries of the nuisance filter. For example, defects that the trained nuisance filter classifies with the smallest confidence may be considered close to a classification boundary and selected for the sample.

The events in the portion include DOIs and nuisance events. In particular, the events are purposefully selected to include both DOIs and nuisance events. For example, the events are selected such that the portion of the events includes events having feature values that are relatively close to a parameter value of the nuisance filter such as a classification boundary. In addition, the selected events preferably have feature values that are both above and below the parameter value of the nuisance filter. As such, when the parameter value of the nuisance filter is a classification boundary, the selected portion of the events will include events on both sides of the classification boundary. The selected portion of the events will therefore include different types of events. When the classification boundary is one that separates nuisance events from DOIs, then the selected portion of the events will include both DOIs and nuisance events.

The computer subsystem(s) are also configured for acquiring the output of the output acquisition subsystem for the sample of the events and classifying the events in the sample based on the acquired output. In this manner, the computer subsystem(s) may be configured for reviewing the events in the sampled portion and classifying them in some manner e.g., automatically classifying them). Classifying the events in the sample is preferably performed in a different manner than applying the nuisance filter as described herein. For example, preferably, classifying the events in the sample is performed with a defect classifying method and/or algorithm that is different than the method and/or algorithm to be used for nuisance filtering. In particular, since the results of classifying the events in the sample may be used, as described further herein, to modify (or tune) the nuisance filter, preferably, the defect classification method and/or algorithm produces defect classification results that are independent of the nuisance filtering. In this manner, the classification of the sampled events will produce results that are suitable for tuning or modifying the nuisance filter.

In one embodiment, the classifying includes determining if the events are DOIs or nuisance events. In addition, the events may be classified as true SEM non-visuals (SNV) (in instances where the system is configured as a SEM and possibly after an event has been analyzed using multiple output acquisition modes on the SEM), one or more known nuisance types (e.g., real defects on the specimen that do not impact yield and thus are considered to be nuisance events from a process monitoring point of view), and/or one or more known defect types (e.g., known DOIs that are important for process monitoring). The classification method and/or algorithm used by the computer subsystem(s) to perform the classifying may also produce an event-level confidence for each of the classifications. In other words, results of the classifying may include a confidence with which each event has been classified. Therefore, the confidence may be used as an estimate of the accuracy of the results of the classifying that are used, as described further herein, as the ground truth for re-tuning the nuisance filter and therefore the inspection process. As such, the confidence may be used as an event-level weighting factor for re-tuning (a relatively high confidence event would carry higher weight in re-tuning).

The computer subsystem(s) are further configured for determining if one or more of the parameters of the nuisance filter should be modified based on results of the classifying. Determining if the parameter(s) of the nuisance filter should be modified can be based on the results of the classifying and/or information determined based on the results of the classifying. For example, the results of the classifying can be used to determine an estimate of the nuisance event capture rate of the nuisance filter (or an inspection process that includes the nuisance filtering). That estimate can be compared to the original nuisance rate, and depending on how much they differ, different actions can be taken. For example, if the estimate and the original nuisance rate are different by greater than a predetermined amount or range, then the nuisance filter parameter(s) may be altered as described further herein. However, if the estimate and the original nuisance rate are different by less than the predetermined amount or range, then the computer subsystem(s) may determine that the nuisance filter parameter(s) do not need to be altered. In this manner, the computer subsystem(s) may perform an inspection result stability estimate (e.g., to see if the nuisance event capture rate is relatively stable) before doing any retuning described further herein. (These estimates can be based on existing sampling strategies employed during production monitoring and therefore do not involve any additional tool time on the review station.)

In a further embodiment, the results of the classifying used for the determining include information for which of the events are classified as DOIs and which of the events are classified as nuisance events, and the determining includes determining a DOI capture rate of the nuisance filter based on the information, comparing the DOI capture rate to a desired DOI capture rate, and determining that the one or more of the parameters should be modified if the DOI capture rate is lower than the desired DOI capture rate. For example, the information for which of the events are classified as DOIs and nuisance events along with their respective feature values may be used to determine which of the DOIs would be identified as such by the nuisance filter (e.g., by comparing the feature values of the DOIs to a classification boundary value of the nuisance filter to determine how many of the DOIs would be erroneously filtered out of the inspection results by the nuisance filter). The DOI capture rate determined for the sample of the events may be used to estimate a DOI capture rate for the entire population of events. That DOI capture rate can be compared to the desired capture rate and when the estimated DOI capture rate is lower than desired, the computer subsystem(s) may determine that the one or more of the parameters of the nuisance filter should be modified. In this manner, the criteria for re-tuning may include a target DOI capture rate.

In an additional embodiment, the results of the classifying used for the determining include information for which of the events are classified as DOIs and which of the events are classified as nuisance events, and the determining includes determining a nuisance event capture rate of the nuisance filter based on the information, comparing the nuisance event capture rate to a desired nuisance event capture rate, and determining that the one or more of the parameters should be modified if the nuisance event capture rate is higher than the desired nuisance event capture rate. For example, the criteria for re-tuning may include a target nuisance rate (possibly in combination with optimal DOI capture). These steps may be performed as described above except that the nuisance event capture rate is determined and used instead of a DOI capture rate.

In one embodiment, the classifying includes determining if the events are DOIs or nuisance events and determining a confidence with which each of the events are determined to be the DOIs or the nuisance events. Determining if the events are DOIs or nuisance events may be performed in any suitable manner using any suitable classification method and/or algorithm. The confidence with which each of the events are determined to be DOIs or nuisance events may be output by the classification method and/or algorithm as described further above.

In one such embodiment, the results of the classifying used for the determining include the confidence determined for one or more of the events. For example, the computer subsystem(s) can determine if the parameter(s) of the nuisance filter such as cut-lines and classification boundaries need to be retuned based on the classification assigned to each of the events and the confidence with which each event was classified by the classifying described herein. In one such example, if the confidence with which some of the events have been classified is relatively low, then those classifications may be given less weight in determining if the one or more of the parameters of the nuisance filter should be modified than classifications determined with relatively high confidence.

In another such embodiment, the results of the classifying used for the modifying described further herein include the confidence determined for one or more of the events. For example, the parameter(s) of the nuisance filter such as cut-lines and classification boundaries can be re-tuned based on the classification assigned to each of the events and the confidence with which each event was classified by the classifying. In one such example, if the confidence with which some of the events have been classified is relatively low, then those classifications may be given less weight in determining the modified one or more of the parameters of the nuisance filter than classifications determined with relatively high confidence.

The computer subsystem(s) are also configured for, when it is determined that the one or more of the parameters of the nuisance filter should not be modified, applying the nuisance filter to the results of the inspection for the specimen to generate final inspection results for the specimen. In this manner, the inspection may be completed when a system other than the one that performed the inspection applies the nuisance filter to the results of the inspection. As such, the application of the nuisance filter to the inspection results may be postponed until after additional post-inspection processing (e.g., SEM review). The nuisance filter may be applied to the inspection results in any suitable manner. In addition, the final inspection results may be generated in any suitable manner and may have any suitable format known in the art.

The computer subsystem(s) are further configured for, when it is determined that the one or more parameters of the nuisance filter should be modified, modifying the nuisance filter by modifying the one or more of the parameters of the nuisance filter based on the results of the classifying and applying the modified nuisance filter to the results of the inspection for the specimen to generate the final inspection results for the specimen. For example, the nuisance filter may be re-tuned using the newly classified events. Re-tuning the nuisance later may include changing the values for one or more parameters of the nuisance filter such as values for classification boundaries or cutlines. In general, however, re-tuning the nuisance filter may not include altering the parameters themselves or any template of the nuisance filter. For example, the retuning of the nuisance filter will typically not include changing the structure of the nuisance filter or the general operation or function of the nuisance filter. In addition, modifying the one or more parameters of the nuisance later will not, in general, include replacing the nuisance filter with a different nuisance filter. In addition, after re-tuning is finished, the nuisance filter can be applied to the inspection results to filter out nuisance defects and produce the final inspection result for the specimen. Therefore, the re-tuned nuisance filter can be applied to the results of the inspection and the results can be saved in an inspection results file. In this manner, the inspection may be completed when a system other than the one that performed the inspection applies the modified nuisance filter to the results of the inspection. As such, the application of the nuisance filter to the inspection results may be postponed until after additional post-inspection processing (e.g., SEM review). The modified nuisance filter may be applied to the inspection results in any suitable manner. In addition, the final inspection results may be generated in any suitable manner and may have any suitable format known in the art.

In one embodiment, the one or more computer subsystems are further configured for, when it is determined that the one or more of the parameters of the nuisance filter should be modified, modifying a recipe used for the inspection to replace the nuisance filter in the recipe with the modified nuisance filter. For example, the nuisance filter may be updated with the newly tuned nuisance filter after each inspection and/or after each nuisance filter modification, and the updated nuisance filter can be used as the initial nuisance filter for the subsequent hybrid inspection. A "hybrid" inspection as that term is used herein refers to one in which the inspection is started on one tool (e.g., an optical inspection tool), but the inspection is finalized on another tool (e.g., a SEM tool) using the method described herein. In this manner, the specimen inspection is performed using two tools (e.g., an optical tool and an electron beam tool). Therefore, the inspection may involve different modalities (e.g., optical and SEM) thereby rendering it a "hybrid" inspection.

In some embodiments, the computer subsystem(s) are configured for, when it is determined that the one or more of the parameters of the nuisance filter should be modified, determining if generating the sample, acquiring the output, classifying the events, and the determining should be performed for another sample of the events based on how much the one or more of the parameters are modified. In this manner, the computer subsystem(s) may be configured for assessing the need for additional sampling based on how much the parameter(s) such as classification boundaries move. As such, the computer subsystem(s) may sample more events to reduce the uncertainties of the results of the previously performed steps. For example, if the cut-lines, classification boundaries, or other parameters of the nuisance filter are moved significantly, an additional set of defects may be needed for validation and/or additional tuning. These steps may be repeated until a desired confidence is reached and/or the time and/or resources allocated for the process is exhausted. Confidence in this instance refers to the confidence that the re-tuning has achieved the target stability criteria. In this manner, the functions and steps described herein may be iterated until the desired stability is reached. These criteria (confidence and/or stability) may be used to make the inspection more stable, meaning more independent of process variations than those based on a fixed recipe. The stability may be measured in terms of nuisance rate and/or true DOI capture rate. In particular, any sampling such as that described herein carries inherent statistical errors as well as some probability of misclassification errors. The combination of these errors can be used to determine a confidence that the re-tuning has achieved a target stability criteria that is within a predetermined range. As such, iterations of sampling, classifying, and tuning may be performed to achieve desired performance of the nuisance filter.

In another embodiment, the computer subsystem(s) are configured for, when it is determined that the one or more of the parameters of the nuisance filter should be modified, determining if generating the sample, acquiring the output, classifying the events, and the determining should be performed for another sample of the events based on the results of the classifying. For example, the computer subsystem(s) may be configured for assessing the need for additional sampling based on how reliable the classification is. In one such example, if the classification comes with relatively low confidence, more examples of the events may be sampled and classified to achieve a higher confidence on classification. As such, the computer subsystem(s) may sample more events to reduce the uncertainties of the results of the previously performed functions or steps. Specifically, events with low classification confidence may be sampled to determine the ground truth and thus increase the classification confidence most substantially with smallest sample size. These functions or steps may be repeated until a desirable confidence is reached and/or the time and/or resources allocated for the process is exhausted. In this manner, the functions or steps described herein may be iterated until the desired confidence is reached. As such, iterations of sampling, classifying, and tuning may be performed to achieve desired performance of the nuisance filter.

In a further embodiment, the computer subsystem(s) are configured for, when it is determined that the one or more of the parameters of the nuisance filter should be modified, determining if generating the sample, acquiring the output, classifying the events, and the determining should be performed for another sample of the events and, when it is determined that generating the sample, acquiring the output, classifying the events, and the determining should be performed for the other sample, altering one or more parameters used for the selecting. For example, once it has been determined that the computer subsystem(s) should perform the various functions or steps again for another sample, the sampling strategy may be refined and then another sample can be generated using the refined strategy. In one such example, in subsequent iteration(s), the computer subsystem(s) may sample more around the new cut line positions, classification boundary values, or other parameter values. How much more of the sampling is performed may be established by confidence criteria on the new parameter values, e.g., the fraction of classified defects to unclassified defects in some region around the parameter values. In addition, the subsequent iteration(s) may sample more to improve classification confidence. For example, if a correlation can be established between the low confidence classified events and the features reported by inspection, the sampling can be targeted to that region in the feature space. In this manner, the increased sampling can lower statistical errors associated with classification uncertainty near the classification boundary, which can lead to creation of a better classifier (i.e., a classifier capable of producing classifications with higher confidence). In addition, the last sampling iteration is performed after good classification results have been established to estimate the nuisance rate and DOI capture rate of the new nuisance filter. The confidence of this estimate is controlled by the amount of sampling of the last iteration.

In some embodiments, the nuisance filter is tuned prior to the inspection of the specimen based on results generated with a training specimen. For example, an optical or other inspection system may tune a nuisance filter on a training wafer. In this manner, the embodiments described herein may be configured for re-tuning a nuisance filter in a perturbative manner. In other words, since the nuisance filter has been used for inspection of other specimens, the tuning of the nuisance filter is not started from scratch for each specimen. Instead, the tuning of the nuisance filter can be started from the nuisance filter parameters that were known to work well on previous specimens. As such, the computer subsystem(s) described herein can combine the results of the classifying described herein with the information obtained from specimens used previously for tuning and/or setup and/or specimens whose inspection results were previously filtered with the nuisance filter. In this manner, the new parameters for the nuisance filtering can be looked for in the neighborhood of the optimal parameters from previous specimens, which can be used again if the process does not fluctuate between specimens at all. The perturbative tuning of the nuisance filters described herein can increase their reliability and robustness.

In another embodiment, the nuisance filter is tuned prior to the inspection of the specimen based on results generated with a training set of defects, and modifying the nuisance filter includes adding information for the events in the sample and the results of the classifying to the training set of defects to generate a modified training set and modifying the one or more parameters of the nuisance filter based on the modified training set. In this manner, the embodiments described herein may combine prior knowledge obtained during supervised tuning of the nuisance filter during initial recipe creation with dynamic information obtained by the embodiments described herein. For example, the original training set used to set up the nuisance filter may be kept and the content of the training set may be modified with the results of the classifying described herein. The modified training set may then be used to retune the nuisance filter. In addition, differences between the original training set and the modified training set may be used to determine if retuning of the nuisance filter should be performed. For example, the original tuned nuisance filter can be applied to the results of the hot inspection described herein. The results of applying that nuisance filter (e.g., the events determined to be DOIs by the nuisance filter) can be sampled. If the nuisance rate in the DOI results is the same or roughly the same as that determined using the original training set, then the computer subsystem(s) described herein may determine that there is no need to retune the nuisance filter. Alternatively, the original training set may be scrapped in favor of the new training set (e.g., generated from the sampled events and the results of the classifying performed for the sampled events) and that new training set can be used for retuning the nuisance filter.

Although some embodiments are described herein as re-tuning previously tuned nuisance filters, there are different variants of the hybrid tuning process, one of which may rely on complete retuning of the nuisance filters (e.g., starting the tuning process from scratch, ignoring the previous solutions), instead of performing perturbative corrections to the initial filter. For example, an optical inspection system may create a recipe for a hot inspection and generate hot inspection results without creating or tuning a nuisance filter and without applying a nuisance filter to the hot inspection results. A template or representation of a nuisance titter such as a level-based tree representation may be created or acquired by the embodiments described herein. The computer subsystem(s) may then create an initial nuisance filter based on the template using the hot inspection results. The sampling described herein may then be replaced with sampling as would be performed during initial tuning of a nuisance filter (where the parameter(s) of the nuisance filter are unknown and so the sampling cannot be focused to the event features near the values of the nuisance filter parameters as described further herein). The sampled defects may then be classified by the computer subsystem(s) as described herein. In addition, the computer subsystem(s) may tune the nuisance filter using the classified defects. The computer subsystems(s) may also perform other functions described herein such as refining the sampling strategy based on the results of the tuning and/or applying the tuned nuisance filter to the inspection results to produce the final inspection results.

In some embodiments, the computer subsystem(s) are further configured for generating the final inspection results by including the results of the classifying in the final inspection results regardless of results of applying the nuisance filter or the modified nuisance filter to the results of the inspection for the specimen. For example, useful information (e.g., SEM images, classification results such as class codes, and confidences) is acquired by the embodiments described herein. Therefore, it makes sense to leverage that information as the nuisance filter is applied. For example, when the classification described herein identifies high confidence DOI, even if the nuisance filter or the modified nuisance filter wants to filter out those high confidence DOI, the high confidence DOI can be included in the final inspection results. In other words, the computer subsystem(s) may inject defects into the final inspection results that the nuisance filter rejects as nuisance but the classification performed as described herein classifies as DOIs with relatively high confidence.

In one such example, the classifying described herein may identify an important DOI such as a small bridge. However, a perfectly tuned (or retuned) nuisance filter may not be able to identify that small bridge defect as a DOI (e.g., when optimization of the parameters of the nuisance filter do not lead to optimum filtering of all nuisance events and/or optimum retention of all DOIs as such). Therefore, the computer subsystem(s) may evaluate the results of applying the nuisance filter or the modified nuisance filter to the results of the inspection of the specimen. If the small bridge DOI is not included in the final inspection results produced by applying the nuisance filter or modified nuisance filter, the computer subsystem(s) may alter the final inspection results such that the final inspection results include the small bridge defect with its corresponding classification information. In this manner, the nuisance filter results can be ignored and/or overruled when it comes to high confidence DOI. As such, the DOI capture rate for the inspection can be improved.

In a similar manner, high confidence nuisance defects (as determined by the classifying performed as described herein) can be filtered out even if these high confidence nuisance defects are identified as DOI by the nuisance filter. In other words, the computer subsystem(s) can remove defects from the inspection results that violate the nuisance filter boundaries and that were determined to be nuisance by the classification with relatively high confidence. In this manner, the nuisance filter results can be ignored and/or overruled when it comes to high confidence nuisance events. As such, the nuisance event capture rate for the inspection can be improved.

In an additional embodiment, the computer subsystem(s) are configured for determining a difference between the modified nuisance filter and the nuisance filter and sending an alert to a user when the difference is outside of a predetermined range of values for the difference. For example, the results produced by the embodiments described herein may be used to monitor stability of the recipe used for the inspection and/or to monitor for noise floor shifts in the output generated in the inspection. In other words, the information obtained during the dynamic nuisance filter tuning can be used for the purpose of inspection stability monitoring. In one such example, as a byproduct of the nuisance filter tuning, information about the movement of the filter parameters can be recorded along with estimates of the static and dynamic nuisance rate and DOI counts. This information can be used for quantitative monitoring of inspection stability and alert users to abrupt or systematic shifts in the noise floor.

In a further embodiment, the computer subsystem(s) are configured for acquiring parameters for defect detection performed in the inspection of the specimen and determining if one or more of the parameters for the defect detection should be modified based on the results of the classifying. For example, the embodiments described herein may be configured for performing not only dynamic tuning of nuisance filters, but also for dynamic tuning of detection thresholds. In one such example, the output of the inspection system generated for the events classified as DOIs and nuisance events by the embodiments described herein (e.g., inspector images for classified DOI and nuisance events) can be used to determine if the parameters for defect detection, which were applied to the output, can be modified to reduce the detection of nuisance events and/or to increase the detection of DOIs. The defect detection parameter(s) can then be modified based on the output generated by the inspection system for the classified events, the classifications generated by the embodiments described herein, and any other information described herein to modify the defect detection parameter values. Modifying the defect detection parameters may be further performed as described herein with respect to modifying the nuisance filter parameters, and other steps described herein (performed for the nuisance filter) may be also performed for the detect detection parameters.

In another embodiment, the computer subsystem(s) are configured for acquiring parameters for defect classification performed in the inspection of the specimen and determining if one or more of the parameters for the defect classification performed in the inspection of the specimen should be modified based on the results of the classifying. For example, the embodiments described herein may be configured for performing not only dynamic tuning of nuisance filters, but also for dynamic tuning of defect classification. In this case, the initial tuned classifier can be used on the optical inspector and the dynamic classification from the embodiments described herein can be used to retune the classifier for each specimen.

The embodiments described herein have a number of advantages over other currently used static nuisance filters applied to optical inspections today. For example, the embodiments described herein improve on the static nuisance filters by combining prior knowledge obtained during supervised tuning of the nuisance filters during initial recipe creation with dynamic information obtained by the embodiments described herein. In addition, the final inspection results may be sent to a user or a user yield management system only after the dynamic update of the optical inspection. Furthermore, the embodiments described herein improve the stability of inspection and enable quantitative monitoring of noise floors of inspection. Enabling and/or ensuring the stability of inspection is particularly important since fabs use inspection to monitor their processes through statistical process control (SPC). SPC inherently requires the inspection of specimens to be stable over time to allow establishment of a statistical baseline from which to measure process changes. The embodiments described herein can also perform the tuning of the nuisance filter without user intervention since all of the steps and functions described herein can be performed automatically. In addition, the embodiments described herein can minimize the sample size for the output acquisition and classification steps through the use of prior information obtained from previous specimen(s) and from the inspection recipe setup phase. This sample minimization can provide a huge benefit because it minimizes the tool time requirements needed for acquiring the output (especially when the tool used to acquire the output is a SEM).

The embodiments described herein may perform the functions described herein as often as desired. For example, the computer subsystem(s) may perform the functions or steps for determining if the nuisance filter needs to be retuned (and the subsequent retuning) every time that a specimen is inspected. However, the computer subsystem(s) may perform the functions or steps described herein less often if the processes used to form the specimen are relatively stable, which should produce relatively stable inspection results and thereby relatively stable nuisance filtering results. In this manner, the steps described herein can be performed at a frequency that reflects the stability of the processes used to form the specimen (e.g., less often for more stable processes and more often for less stable processes).

Another embodiment relates to a computer-implemented method for generating inspection results for a specimen with an adaptive nuisance filter. The method includes steps for each of the functions of the computer subsystem(s) described above.

Each of the steps of the method may be performed as described further herein. The method may also include any other step(s) that can be performed by the output acquisition subsystem and/or computer subsystem(s) or system(s) described herein. The steps of the method are performed by one or more computer subsystems, which may be configured according to any of the embodiments described herein. In addition, the method described above may be performed by any of the system embodiments described herein.

Figure 3:
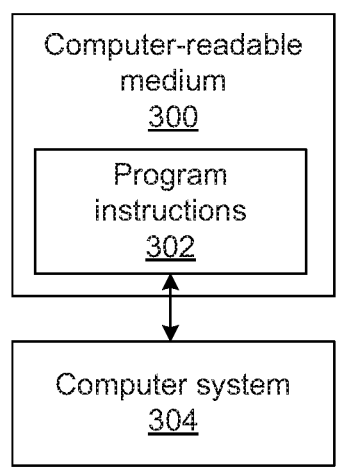
FIG. 3 is a block diagram illustrating one embodiment of a non-transitory computer-readable medium storing program instructions executed on a computer system for performing one or more of the computer-implemented methods described herein.

An additional embodiment relates to a non-transitory computer-readable medium storing program instructions executed on a computer system for performing a computer-implemented method for generating inspection results for a specimen with an adaptive nuisance filter. One such embodiment is shown in FIG. 3. In particular, as shown in FIG. 3, non-transitory computer-readable medium 300 includes program instructions 302 executable on computer system 304. The computer-implemented method may include any step(s) of any method(s) described herein.

Program instructions 302 implementing methods such as those described herein may be stored on computer-readable medium 300. The computer-readable medium may be a storage medium such as a magnetic or optical disk, a magnetic tape, or any other suitable non-transitory computer-readable medium known in the art.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), SSE (Streaming SIMD Extension) or other technologies or methodologies, as desired.

Computer system 304 may be configured according to any of the embodiments described herein.

All of the methods described herein may include storing results of one or more steps of the method embodiments in a computer-readable storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc.

Further modifications and alternative embodiments of various aspects of the invention will be apparent to those skilled in the art in view of this description. For example, methods and systems for generating inspection results for a specimen with an adaptive nuisance filter are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to generate inspection results for a specimen with an adaptive nuisance filter, comprising:

an output acquisition subsystem comprising at least an energy source and a detector, wherein the energy source is configured to generate energy that is directed to a specimen, and wherein the detector is configured to detect energy from the specimen and to generate output responsive to the detected energy; and one or more computer subsystems configured for:

acquiring results of an inspection of the specimen and parameters of a nuisance filter for the inspection, wherein the results comprise values for one or more features for events detected during the inspection, and wherein the values are determined during the inspection;

generating a sample of the events by selecting a portion of the events having the values for at least one of the one or more features that are closer to at least one value of at least one of the parameters of the nuisance filter than the values for the at least one of the one or more features of another portion of the events;

acquiring the output of the output acquisition subsystem for the sample of the events;

classifying the events in the sample based on the acquired output;

determining if one or more of the parameters of the nuisance filter should be modified based on results of the classifying;

when it is determined that the one or more of the parameters of the nuisance filter should not be modified, applying the nuisance filter to the results of the inspection for the specimen to generate final inspection results for the specimen; and when it is determined that the one or more of the parameters of the nuisance filter should be modified:

modifying the nuisance filter by modifying the one or more of the parameters of the nuisance filter based on the results of the classifying; and applying the modified nuisance filter to the results of the inspection for the specimen to generate the final inspection results for the specimen.

2. The system of claim 1, wherein the events in the portion comprise defects of interest and nuisance events.

3. The system of claim 1, wherein the inspection of the specimen is performed by an optical inspection system.

4. The system of claim 1, wherein the inspection of the specimen is performed with another output acquisition subsystem having a configuration different than the output acquisition subsystem.

5. The system of claim 1, wherein the inspection of the specimen is performed with defect detection parameters selected such that the events detected by the inspection comprise a substantial amount of nuisance events.

6. The system of claim 1, wherein the at least one of the parameters of the nuisance filter comprises a boundary separating one type of the events from another type of the events.

7. The system of claim 1, wherein the inspection does not comprise applying the nuisance filter to any of the results of the inspection.

8. The system of claim 1, wherein the one or more computer subsystems are further configured for, when it is determined that the one or more of the parameters of the nuisance filter should be modified, modifying a recipe used for the inspection to replace the nuisance filter in the recipe with the modified nuisance filter.

9. The system of claim 1, wherein the one or more computer subsystems are further configured for, when it is determined that the one or more of the parameters of the nuisance filter should be modified, determining if the generating, acquiring the output, classifying, and determining should be performed for another sample of the events based on how much the one or more of the parameters are modified.

10. The system of claim 1, wherein the one or more computer subsystems are further configured for, when it is determined that the one or more of the parameters of the nuisance filter should be modified, determining if the generating, acquiring the output, classifying, and determining should be performed for another sample of the events based on the results of said classifying.

11. The system of claim 1, wherein the one or more computer subsystems are further configured for, when it is determined that the one or more of the parameters of the nuisance filter should be modified, determining if the generating, acquiring the output, classifying, and determining should be performed for another sample of the events and, when it is determined that the generating, acquiring the output, classifying, and determining should be performed for the other sample, altering one or more parameters used for said selecting.

12. The system of claim 1, wherein the classifying comprises determining if the events are defects of interest or nuisance events.

13. The system of claim 1, wherein the classifying comprises determining if the events are defects of interest or nuisance events and determining a confidence with which each of the events are determined to be the defects of interest or the nuisance events, and wherein the results of the classifying used for the determining comprise the confidence determined for one or more of the events.

14. The system of claim 1, wherein the classifying comprises determining if the events are defects of interest or nuisance events and determining a confidence with which each of the events are determined to be the defects of interest or the nuisance events, and wherein the results of the classifying used for the modifying comprise the confidence determined for one or more of the events.

15. The system of claim 1, wherein the results of the classifying used for the determining comprise information for which of the events are classified as defects of interest and which of the events are classified as nuisance events, and wherein the determining comprises determining a defects of interest capture rate of the nuisance filter based on the information, comparing the defects of interest capture rate to a desired defects of interest capture rate, and determining that the one or more of the parameters should be modified if the defects of interest capture rate is lower than the desired defects of interest capture rate.

16. The system of claim 1, wherein the results of the classifying used for the determining comprise information for which of the events are classified as defects of interest and which of the events are classified as nuisance events, and wherein the determining comprises determining a nuisance event capture rate of the nuisance filter based on the information, comparing the nuisance event capture rate to a desired nuisance event capture rate, and determining that the one or more of the parameters should be modified if the nuisance event capture rate is higher than the desired nuisance event capture rate.

17. The system of claim 1, wherein the nuisance filter is tuned prior to the inspection of the specimen based on results generated with a training specimen.

18. The system of claim 1, wherein the nuisance filter is tuned prior to the inspection of the specimen based on results generated with a training set of defects, and wherein modifying the nuisance filter comprises adding information for the events in the sample and the results of the classifying to the training set of defects to generate a modified training set and modifying the one or more of the parameters of the nuisance filter based on the modified training set.

19. The system of claim 1, wherein the one or more computer subsystems are further configured for generating the final inspection results by including the results of the classifying in the final inspection results regardless of results of applying the nuisance filter or the modified nuisance filter to the results of the inspection for the specimen.

20. The system of claim 1, wherein the one or more computer subsystems are further configured for determining a difference between the modified nuisance filter and the nuisance filter and sending an alert to a user when the difference is outside of a predetermined range of values for the difference.

21. The system of claim 1, wherein the one or more computer subsystems are further configured for acquiring parameters for defect detection performed in the inspection of the specimen and determining if one or more of the parameters for the defect detection should be modified based on the results of the classifying.

22. The system of claim 1, wherein the one or more computer subsystems are further configured for acquiring parameters for defect classification performed in the inspection of the specimen and determining if one or more of the parameters for the defect classification performed in the inspection of the specimen should be modified based on the results of the classifying.

23. The system of claim 1, wherein the specimen comprises a wafer.

24. The system of claim 1, wherein the energy directed to the specimen comprises light, and wherein the energy detected from the specimen comprises light.

25. The system of claim 1, wherein the energy directed to the specimen comprises electrons, and wherein the energy detected from the specimen comprises electrons.

26. A non-transitory computer-readable medium, storing program instructions executed on a computer system for performing a computer-implemented method for generating inspection results for a specimen with an adaptive nuisance filter, wherein the computer-implemented method comprises:
acquiring results of an inspection of a specimen and parameters of a nuisance filter for the inspection, wherein the results comprise values for one or more features for events detected during the inspection, and wherein the values are determined during the inspection;
generating a sample of the events by selecting a portion of the events having the values for at least one of the one or more features that are closer to at least one value of at least one of the parameters of the nuisance filter than the values for the at least one of the one or more features of another portion of the events;
acquiring output of an output acquisition subsystem for the sample of the events, wherein the output acquisition subsystem comprises at least an energy source and a detector, wherein the energy source is configured to generate energy that is directed to the specimen, and wherein the detector is configured to detect energy from the specimen and to generate the output responsive to the detected energy;
classifying the events in the sample based on the acquired output;
determining if one or more of the parameters of the nuisance filter should be modified based on results of the classifying;
when it is determined that the one or more of the parameters of the nuisance filter should not be modified, applying the nuisance filter to the results of the inspection for the specimen to generate final inspection results for the specimen; and
when it is determined that the one or more of the parameters of the nuisance filter should be modified:
modifying the nuisance filter by modifying the one or more of the parameters of the nuisance filter based on the results of the classifying; and
applying the modified nuisance filter to the results of the inspection for the specimen to generate the final inspection results for the specimen, wherein acquiring the results, generating the sample, acquiring the output, classifying the events, said determining, applying the nuisance filter, modifying the nuisance filter, and applying the modified nuisance filter are performed by one or more computer subsystems.

27. A computer-implemented method for generating inspection results for a specimen with an adaptive nuisance filter, comprising:
acquiring results of an inspection of a specimen and parameters of a nuisance filter for the inspection, wherein the results comprise values for one or more features for events detected during the inspection, and wherein the values are determined during the inspection;
generating a sample of the events by selecting a portion of the events having the values for at least one of the one or more features that are closer to at least one value of at least one of the parameters of the nuisance filter than the values for the at least one of the one or more features of another portion of the events;
acquiring output of an output acquisition subsystem for the sample of the events, wherein the output acquisition subsystem comprises at least an energy source and a detector, wherein the energy source is configured to generate energy that is directed to the specimen, and wherein the detector is configured to detect energy from the specimen and to generate the output responsive to the detected energy;
classifying the events in the sample based on the acquired output;
determining if one or more of the parameters of the nuisance filter should be modified based on results of the classifying;
when it is determined that the one or more of the parameters of the nuisance filter should not be modified, applying the nuisance filter to the results of the inspection for the specimen to generate final inspection results for the specimen; and
when it is determined that the one or more of the parameters of the nuisance filter should be modified:
modifying the nuisance filter by modifying the one or more of the parameters of the nuisance filter based on the results of the classifying; and
applying the modified nuisance filter to the results of the inspection for the specimen to generate the final inspection results for the specimen,
wherein acquiring the results, generating the sample, acquiring the output, classifying the events, said determining, applying the nuisance filter, modifying the nuisance filter, and applying the modified nuisance filter are performed by one or more computer subsystems, and wherein the one or more computer subsystems are configured to perform acquiring the results, generating the sample, acquiring the output, classifying the events, said determining, applying the nuisance filter, modifying the nuisance filter, and applying the modified nuisance filter by executing program instructions stored on a non-transitory computer-readable medium.

* * * * *